United States Patent
Bowen et al.

(10) Patent No.: US 8,381,724 B2
(45) Date of Patent: *Feb. 26, 2013

(54) METHOD AND APPARATUS FOR MONITORING AND CONTROLLING A MEDICAL DEVICE

(75) Inventors: Kevin Bowen, Pittsburgh, PA (US); Daniel Jonczak, Greensburg, PA (US); Gregory Yurko, Murrysville, PA (US); Douglas M. Mechlenburg, Pittsburgh, PA (US); Winslow K. Duff, Export, PA (US); Mark D'Angelo, Harrison City, PA (US)

(73) Assignee: RIC Investments, LLC, Wilmington, DE (US)

(*) Notice: Subject to any disclaimer, the term of this patent is extended or adjusted under 35 U.S.C. 154(b) by 1172 days.

This patent is subject to a terminal disclaimer.

(21) Appl. No.: 11/796,786

(22) Filed: Apr. 30, 2007

(65) Prior Publication Data

US 2007/0209662 A1 Sep. 13, 2007

Related U.S. Application Data

(63) Continuation of application No. 09/698,743, filed on Oct. 27, 2000, now Pat. No. 7,225,809.

(60) Provisional application No. 60/162,677, filed on Nov. 1, 1999.

(51) Int. Cl.
*A61M 16/00* (2006.01)
*A62B 7/00* (2006.01)
(52) U.S. Cl. .................. 128/204.21; 128/204.18
(58) Field of Classification Search ............ 128/204.21, 128/204.18, 204.23, 204.22
See application file for complete search history.

(56) References Cited

U.S. PATENT DOCUMENTS

| | | | |
|---|---|---|---|
| 4,627,860 A | 12/1986 | Rowland |
| 4,890,235 A | 12/1989 | Reger et al. |
| 5,036,852 A | 8/1991 | Leishman |
| 5,044,362 A | 9/1991 | Younes |
| 5,060,514 A | 10/1991 | Aylsworth |
| 5,107,830 A | 4/1992 | Younes |
| 5,148,802 A | 9/1992 | Sanders |
| 5,203,343 A | 4/1993 | Axe |
| 5,313,820 A | 5/1994 | Aylsworth |
| 5,313,937 A | 5/1994 | Zdrojkowski |
| 5,369,979 A | 12/1994 | Aylsworth et al. |

(Continued)

FOREIGN PATENT DOCUMENTS

| EP | 0 575 256 A1 | 12/1993 |
|---|---|---|
| GB | 2 334 805 A | 9/1999 |

(Continued)

OTHER PUBLICATIONS

Smart Trace Modem System, pp. 5, 15-15 and 2 Figs., Aug. 9, 1998.

(Continued)

*Primary Examiner* — Justine Yu
*Assistant Examiner* — Valerie L Skorupa
(74) *Attorney, Agent, or Firm* — Michael W. Haas

(57) ABSTRACT

A medical device, such as pressure support system, and a method of communicating with such a device using an information storage device. The information storage device, in one embodiment, is adapted to be provided in a slot in the medical device so that information for controlling the operating of the pressure support device can be read from the information storage device, information regarding the usage and/or operation of the pressure support device can be written to the information storage device, or both operations can be performed.

13 Claims, 9 Drawing Sheets

U.S. PATENT DOCUMENTS

| | | | |
|---|---|---|---|
| 5,398,682 A | 3/1995 | Lynn | |
| 5,433,193 A | 7/1995 | Sanders | |
| 5,452,621 A | 9/1995 | Aylesworth et al. | |
| 5,458,137 A | 10/1995 | Axe | |
| 5,492,113 A | 2/1996 | Estes | |
| RE35,294 E | 7/1996 | Vasquez | |
| 5,535,738 A | 7/1996 | Estes | |
| 5,540,219 A * | 7/1996 | Mechlenburg et al. | 128/204.23 |
| 5,549,106 A | 8/1996 | Gruenke et al. | |
| 5,551,418 A | 9/1996 | Estes | |
| 5,551,436 A | 9/1996 | Yago | |
| 5,560,353 A | 10/1996 | Willemot et al. | |
| 5,590,648 A | 1/1997 | Mitchell et al. | |
| 5,598,838 A | 2/1997 | Servidio et al. | |
| 5,605,151 A | 2/1997 | Lynn | |
| 5,632,269 A | 5/1997 | Zdrojkowski | |
| 5,644,444 A | 7/1997 | Braithwaite et al. | |
| 5,645,053 A | 7/1997 | Remmers | |
| 5,682,878 A | 11/1997 | Ogden | |
| 5,692,497 A | 12/1997 | Schnitzer et al. | |
| 5,694,923 A | 12/1997 | Hete | |
| 5,701,883 A | 12/1997 | Hete et al. | |
| 5,706,801 A | 1/1998 | Remes et al. | |
| 5,762,064 A | 6/1998 | Polvani | |
| 5,794,615 A | 8/1998 | Estes | |
| 5,803,065 A | 9/1998 | Zdrojkowski | |
| 5,803,066 A | 9/1998 | Rapoport et al. | |
| 5,823,187 A | 10/1998 | Estes et al. | |
| 5,836,989 A | 11/1998 | Shelton | |
| 5,871,564 A | 2/1999 | McCombs | |
| 5,878,744 A | 3/1999 | Pfeiffer | |
| 5,881,723 A | 3/1999 | Wallace et al. | |
| 5,890,490 A | 4/1999 | Aylsworth et al. | |
| 5,891,023 A | 4/1999 | Lynn | |
| 5,903,572 A | 5/1999 | Wright | |
| 5,911,219 A | 6/1999 | Aylsworth et al. | |
| 5,927,274 A | 7/1999 | Servidio et al. | |
| 5,954,050 A | 9/1999 | Christopher | |
| 6,017,315 A | 1/2000 | Starr et al. | |
| 6,024,089 A | 2/2000 | Wallace et al. | |
| 6,029,664 A | 2/2000 | Zdrojkowski | |
| 6,047,203 A | 4/2000 | Sackner et al. | |
| 6,087,747 A | 7/2000 | Dhuler | |
| 6,105,573 A | 8/2000 | Delaplane | |
| 6,148,814 A | 11/2000 | Clemmer et al. | |
| 6,273,088 B1 | 8/2001 | Hillsman | |
| 6,349,724 B1 | 2/2002 | Burton et al. | |
| 6,390,091 B1 | 5/2002 | Banner et al. | |
| 6,793,629 B2 | 9/2004 | Rapoport et al. | |
| 7,225,809 B1 * | 6/2007 | Bowen et al. | 128/204.21 |
| 2001/0049263 A1 * | 12/2001 | Zhang | 455/67.1 |

FOREIGN PATENT DOCUMENTS

| | | |
|---|---|---|
| JP | 408292916 | 11/1996 |
| WO | WO 95-32016 | 11/1995 |
| WO | WO 97/16216 | 5/1997 |
| WO | WO 98-33433 | 8/1998 |
| WO | WO 00/53082 | 9/2000 |

OTHER PUBLICATIONS

DeVilbiss SMART Track Modem & IPS, Sales Literature, Sunrise Medical, 1998.

DeVilbiss CPAP Therapy Systems, Sales Literature, Sunrise Medical.

ResMed, The Multi-Purpose Clinical Assistant, Sales Literature, 1999.

* cited by examiner

| PRESCRIPTION DEFINITIONS | | | | |
|---|---|---|---|---|
| CPAP PRESCRIPTION - FORMAT CODE 0 | | | | 112a |
| PARAMETER | SCALE | RANGE | NOTES | |
| CPAP PRESSURE | .1cmH2O | UNIT TYPE SPECIFIC CHOICE: 3-20 cmH2O | IF CPAP PRESSURE < MIN RAMP PRESSURE, THEN MIN RAMP PRESSURE = CPAP PRESSURE | 116 |
| RAMP SHAPE | NA | 0 = NONE 1 = LINEAR | | 118 |
| RAMP TIME | MINUTES | 0-45 | | 120 |
| AUTO ON | NA | 0 = DISABLE 1 = ENABLE | | 122 |
| AUTO OFF | NA | 0 = DISABLE 1 = ENABLE | | 124 |
| AUTO TITRATION PRESCRIPTION - FORMAT CODE 0 | | | | 112b |
| PARAMETER | SCALE | RANGE | NOTES | |
| MINIMUM PRESSURE | .1cmH2O | UNIT TYPE SPECIFIC CHOICE: 3-MAX PR cmH2O | MIN PRESSURE <= MAX PRESSURE | 126 |
| MAXIMUM PRESSURE | .1cmH2O | UNIT TYPE SPECIFIC CHOICE: MIN PR-20 cmH2O | MAX PRESSURE >= MIN PRESSURE | 128 |
| AUTO ON | NA | 0 = DISABLE 1 = ENABLE | | 122 |
| AUTO OFF | NA | 0 = DISABLE 1 = ENABLE | | 124 |
| BILEVEL PRESCRIPTION - FORMAT CODE 0 | | | | 112c |
| PARAMETER | SCALE | RANGE | NOTES | |
| IPAP PRESSURE | .1cmH2O | UNIT TYPE SPECIFIC CHOICE: EPAP-20 cmH2O | IPAP PRESSURE >= EPAP PRESSURE | 130 |
| EPAP PRESSURE | .1cmH2O | UNIT TYPE SPECIFIC CHOICE: 3-IPAP cmH2O | EPAP PRESSURE <= IPAP PRESSURE | 132 |
| RAMP SHAPE | NA | 0 = NONE 1 = LINEAR 0 = BI-LEVEL | | 118' |
| RAMP TIME | MINUTES | 0 - 45 | | 120 |
| AUTO ON | NA | 0 = DISABLE 1 = ENABLE | | 122 |
| AUTO OFF | NA | 0 = DISABLE 1 = ENABLE | | 124 |

FIG. 4

METHOD AND APPARATUS FOR MONITORING AND CONTROLLING A MEDICAL DEVICE

CROSS-REFERENCE TO RELATED APPLICATIONS

This is a continuation of U.S. patent application Ser. No. 09/698,743, filed Oct. 27, 2000, now U.S. Pat. No. 7,225,809, which claims priority under 35 U.S.C. §119(e) from provisional U.S. patent application no. 60/162,677, filed Nov. 1, 1999, the contents of which are incorporated herein by reference

BACKGROUND OF THE INVENTION

1. Field of the Invention

The present invention pertains to a method and apparatus for monitoring and controlling a medical device, and, in particular, to a medical device, such as a pressure support system, in which a removeable information storage device selectively inserts into a slot provided in the medical device for monitoring the use or operation of the device, controlling the operation of the device, or both.

2. Description of the Related Art

Pressure support systems that provide a flow of gas to an airway of a patient at an elevated pressure via a patient circuit to treat a medical disorder are well known. For example, it is known to use a continuous positive airway pressure (CPAP) device to supply a flow of breathing gas at a constant positive pressure to the airway of a patient throughout the patient's breathing cycle. This is done to treat obstructive sleep apnea (OSA), for example. The positive pressure provided by the flow of breathing gas effecting splints the airway, thereby preventing its collapse. Examples of CPAP devices are the REMstar® and Solo® family of pressure support devices manufactured and distributed by Respironics, Inc. of Pittsburgh, PA.

In a typical CPAP device, the operating parameters, such as output pressure, and, hence, the flow of fluid delivered to a patient, is set to a predetermined level prescribed by a qualified caregiver. This level is typically clinically determined for each patient, so that the patient receives pressure support at that an appropriate prescribed level. Most conventional pressure support devices allow the pressure level to be changed by an authorized caregiver or technician, so that a commonly designed CPAP device can be used to provide a pressure support therapy to patients requiring different pressure prescription levels. This also allows the patient's prescription pressure to be changed as the needs of that patient change, without having to replace the patient's existing CPAP device with a new CPAP device. Of course, modifying the prescription level should only to be done under a caregiver's supervision. For this reason, access to the ability to change the prescription pressure levels must be tightly controlled to prevent unauthorized tampering or inadvertent modification of the operating parameters of the CPAP device.

It is also known to provide a positive pressure therapy in which the pressure of the breathing gas delivered to the patient varies with the patient's breathing cycle. A conventional ventilator, such as the Esprit® Ventilator, also manufactured by Respironics, is an example of a pressure support or ventilator system in which the pressure of gas delivered to the patient varies between inspiration and expiration so as to replace or supplement the patient's own ventilation. For purposes of the present invention, the phase "pressure support system" includes any medical device, invasive or non-invasive, that delivers a flow of breathing gas to the airway of a patient, including a ventilator.

It is also known to vary the pressure delivered to the patient between inspiration and expiration to increase the comfort for the spontaneously patient, while providing the desired pressure support therapy. For example, it is known to vary the pressure of the breathing gas delivered to the patient in synchronization with the patient's breathing cycle, so that a lower pressure is delivered to the patient during the expiratory phase of the breathing cycle than is delivered during the inspiratory phase. As a result, the patient receives the necessary pressure support during inspiration to treat their disorder, such as OSA, but is not breathing out against a relatively high pressure during expiration, which can be uncomfortable to some patients. This mode of pressure support is typically referred to as "bi-level" pressure support.

With bi-level pressure support therapy, the patient's inspiratory positive airway pressure (IPAP) and expiratory positive airway pressure (EPAP) are each set to predetermined prescription levels so that the bi-level pressure support device provides the prescribed IPAP and EPAP pressures at the appropriate phase of the breathing cycle. Bi-level pressure support as taught, for example, in U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., the contents of each of which are incorporated by reference into the present invention. It is further known to provide a positive pressure therapy mode in which the pressure provided to the patient changes based on the detected conditions of the patient, such as whether the patient is snoring or experiencing an apnea, hypopnea, upper airway resistance, or a combination thereof. This mode of pressure support is typically referred to as an "auto-titration" mode of pressure support, because the pressure support device itself determines the optimum pressure to deliver to the patient. With this type of pressure support system, the operating parameters of the system, such as the maximum and minimum pressures that can be output by the device, are typically set in advance and can only be adjusted by an authorized caregiver or technician.

An example of an auto-titration pressure support device that adjusts the pressure delivered to the patient based on whether or not the patient is snoring is the Virtuoso® CPAP family of devices manufactured and distributed by Respironics, Inc. This auto-titration pressure support mode is taught in U.S. Pat. Nos. 5,203,343; 5,458,137 and 6,087,747 all to Axe et al., the contents of which are incorporated herein by reference. An example of a pressure support device that actively tests the patient's airway to determine whether obstruction, complete or partial, could occur and adjusts the pressure output to avoid this result is the Tranquility® Auto CPAP device, also manufactured and distributed by Respironics, Inc. This auto-titration pressure support mode is taught in U.S. Pat. No. 5,645,053 to Remmers et al., the content of which is incorporated herein by reference.

Other modes of providing positive pressure to the patient are also known. For example, a proportional assist ventilation (PAV®) mode of pressure support provides a positive pressure therapy in which the pressure of gas delivered to the patient varies with the patient's breathing effort to increase the comfort to the patient. U.S. Pat. Nos. 5,044,362 and 5,107,830 both to Younes, the contents of which are incorporated herein by reference, teach a pressure support device capable of operating in a PAV mode. Proportional positive airway pressure (PPAP) devices deliver breathing gas to the patient based on the flow generated by the patient. U.S. Pat. Nos. 5,535,738; 5,794,615; and 6,105,573 all to Estes et al., the contents of which are incorporated herein by reference, teach a pressure support device capable of operating in a PPAP mode.

Typically, the appropriate mode of pressure support, e.g., CPAP, bi-level, auto-titration, PPAP, PAV, or a combination thereof is determined by the caregiver based on the results of a sleep study or other criteria, such as the patient's ability to tolerate certain types of pressure support or the objectives of the pressure support therapy. The operating parameters of the pressure support device, such as CPAP level, IPAP and EPAP levels in the case of a bi-level pressure support, percent of assistance in the case of a PAV or PPAP device, maximum/minimum pressure in the case of an auto-titration device, are also prescribed, for example, based on the results of sleep study, the conditions of the patient, and/or the goals to be achieved by the pressure support therapy.

Once the appropriate mode of pressure support is established and the appropriate pressure level or levels or percent of assistance are prescribed, the patient receives a pressure support system that is capable of administering the prescribed pressure support mode within the range of prescribed operating parameters. Prior to beginning the pressure support treatment, the pressure support device provider or other caregiver sets the operating parameters of the pressure support device, such as the prescribed pressure level or levels or percent assistance, based on the prescription for that patient.

Other operating parameters that are typically set by the device provider or other caregiver include enabling or disabling additional features of the pressure support device, such as alarms, the ability to provide a time backup breath, and a pressure ramp, which is a feature in which the pressure level provided to the patient is gradually increased over time to allow the patient to fall asleep under a relatively low pressure. The device provider also typically sets the duration of the ramp period as an operating parameter. As with the operating parameters associated with the prescription pressure discussed above, activating, deactivating or altering other features of the pressure support system is preferably and, in many cases, necessarily done by an authorized caregiver or technician under the direction and/or supervision of the physician or other caregiver responsible for that patient.

For purposes of the present invention, "operating mode" refers to the type of pressure support treatment provided to the patient by the pressure support device, e.g., CPAP, bi-level, auto-titration, PPAP, PAV, or a combination thereof. While a great number of pressure support systems can only operate in one mode, some conventional pressure support systems can operate in different pressure support modes depending on how the system is set up. For example, a typical bi-level pressure support system will operate as a CPAP device if the IPAP and EPAP levels are the same. Typically, once a patient is prescribed a mode of pressure support treatment, to minimize cost, he or she will receive a pressure support device that is only capable of operating in that pressure support mode.

Those skilled in the art can also appreciate that a conventional ventilator system is typically capable of operating in different ventilation modes, with each mode representing a different technique for triggering and/or cycling the ventilator. It is common in a ventilator, for the caregiver to be able to select from a variety of modes of ventilation using selection devices provided on the ventilator. Because a ventilator is typically used in a hospital or other highly supervised environment, there is less chance that the patient or others will intentionally or inadvertently alter the operating mode of the system.

The phase "operating parameter" used herein refers to all other variables that can be altered or controlled in each operating mode. For example, in a CPAP device, the CPAP level is considered an operating parameter. In a bi-level device, the IPAP and EPAP levels are operating parameters. In the case of a PAV or PPAP device, the operating parameter is the percent of assistance provided by the device. In an auto-titrating device, the maximum/minimum pressures, amount of pressure change during each pressure increment or decrement, and breathing disorder event detection thresholds are examples, of operating parameters. It is to be understood that this list is not exclusive. Those skilled in the art can appreciate that other features of the pressure support or ventilation system can be controlled by the user, technician, caregiver or others. In general, an operating parameter includes any feature of the system that can be manually controlled directly or indirectly, such as whether to activate the pressure ramp discussed above and the duration of the ramp.

Physically setting the operating mode and/or parameters, including enabling and disabling features of the pressure support device, typically is done by manually setting a switch, dial, knob or other input device on the pressure support device. Depending on the capabilities of the pressure support device, it is also accomplished by downloading the operating mode and/or operating parameters directly into a controller in the pressure support device via a dedicated RS232 port. This assumes, or course, that the pressure support system allows for modification of the operating mode or parameters and can support the selected mode and parameter.

Either of these techniques for setting up the pressure support system require the device provider, technician, or other authorized person to physically open the pressure support device to gain access to the input setting components that are otherwise inaccessible to the patient, to have access to the input devices on the system for changing the mode or parameters using an authentication/authorization protocol, have access to the computer terminal on the device, or any combination thereof. As noted above, the pressure support device is configured such that setting or changing the operating mode and/or operating parameters can only be accomplished by an authorized technician or caregiver. This prevents the patient or others from intentionally or accidentally changing the operating mode and/or parameters, such as the prescription pressure level(s) once they are set by the caregiver. That is, once the operating parameters of the pressure device have been set, the patient begins using the device to treat their breathing disorder and the operating mode and/or parameters remain in effect as long as the patient uses the device. Only a person having the proper knowledge, equipment, training, access codes, etc. can gain access to the ability to alter the operating mode or parameters of the medical device.

It can be appreciated that it may be necessary for the patient to be switched to a different operating mode, different operating parameters, or both over the course of their diagnosis and/or treatment. It can be further appreciated that the operating mode or parameters should only be changed under the supervision of an authorized caregiver. As a result, changing the set up of the pressure support system is a burdensome process requiring an excessive amount of effort from the caregiver, device provider, or other authorized person responsible for servicing the prescribed pressure support system.

For example, it is not uncommon for an OSA sufferer to initially be treated with a CPAP device, and, thereafter, switched to a bi-level device in order to increase their comfort and compliance with the pressure support therapy. Using conventional pressure support systems, this switch requires that the patient receive an entirely new bi-level device in place of the CPAP device. This is obviously expensive and burdensome on the healthcare provider, who must deliver and install the new bi-level system in place of the existing CPAP device. Alternatively, a bi-level device could be prescribed to the patient with the IPAP and EPAP levels set to the same pressure for the CPAP treatment, then changed to different levels for the bi-level treatment. However, this approach is also not practical because, as noted below, changing even the IPAP and/or EPAP prescription levels requires that the authorized person have access to the device, for example, by visiting the patient's home, to make the prescription pressure change.

It is also not uncommon for the need to arise to change the operating parameters of the system. For example, there is often a need to change the prescription pressure output by the pressure support device, the duration of the pressure ramp, or the features of the system, over the course of the patient's support therapy. It can be appreciated from the above-description of how these parameters are set, that changing the operating parameters is a relatively complicated and cumbersome process and cannot be done by the patient. For example, if the patient's initial CPAP or IPAP prescription pressure is too low, increasing the prescription pressure requires that the pressure support device provider or other authorized caregiver visit the patient's home where the unit is located to make the necessary modifications. Of course, the patient can return the pressure support device to the provider to make the changes at their facility. Either scenario imposes a significant burden on the patient, the device provider, or both.

Because each conventional pressure support system is tailored to the needs of one patient and cannot be changed except under the supervision of a caregiver, each patient is, in effect, only able to use the pressure support device that has been tailored to his or her medical needs. That is, each patient has a unique pressures support therapy prescription determined by a caregiver, and the patient receives a pressure support system configured to conform to that prescription. Therefore, in order to receive the prescribed pressure support treatment, the patient must have his or her specifically configured device with them, and not some other pressure support device, because the other pressure support device cannot be readily altered to conform to that patient's prescription. It can be appreciated that this represents a significant burden on the patient, especially if patient travels frequently. In which case, the patient subjects the pressure support device to damage and wear during transportation or must have multiple pressure support systems available, one for home and one for travel.

Of growing importance with respect to pressure support systems is the ability to monitor the patient's use of the prescribed pressure support device, typically referred to as their "compliance" with the prescribed therapy. For example, a cost conscious healthcare provider may require that the compliance data be recorded and monitored before a reimbursement is made. Numerous techniques exist for monitoring and measuring the patient's compliance with the prescribed pressure therapy. However, a difficulty exists in reliably and accurately reporting the compliance data to a caregiver or healthcare provider.

Most conventional pressure support systems generate compliance data and store it in memory for downloading to an external computer via an RS232 port and/or for display on a display screen in the pressure support device. Other conventional pressure support devices increment a compliance meter visible on the unit. These compliance monitoring techniques require that the device provider or other caregiver physically inspect the pressure support device or physically access the device in order to view or download the compliance data.

It is also known to download compliance data from a pressure support device to a central location via a modem. This technique, however, requires that the patient have access to an available telephone jack and be trained in how to configure the system to use the telephone modem. It also requires that the pressure support system include dedicated circuitry, such as an internal modem or a modem jack, so that the modem can be installed on the device for communicating via conventional communication techniques with a central receiving station. It can be appreciated that providing such dedicated components increases the cost and complexity of the pressure support device. Therefore, it is preferable not to include dedicated communication circuitry in every pressure support system, especially if only a small percentage of patients need to monitored this closely. In addition, the data receiving center that accumulates the compliance data via a modem must have the ability to receive, identify and organize the incoming data, which requires a relatively complicated, automated data processing capability.

SUMMARY OF THE INVENTION

Accordingly, it is an object of the present invention to provide a pressure support system that overcomes the shortcomings of conventional pressure support systems. This object is achieved according to one embodiment of the present invention by providing a pressure support system that includes a housing and a pressure generating system provided within the housing for generating a flow of breathing gas. A controller, also disposed within the housing, controls the operation of the pressure generating system. A slot provided in the exterior surface of the housing is sized and configured for selectively receiving an information storage device, which is small, light weight, and easily transported, for example, in the mail. A terminal associated with the slot enables the information storage device to communicate with the controller via the terminal when the information storage device is in the slot. This configuration enables the controller to read information from the information storage device, write information to the information storage device, or both when the information storage device is in the slot. In this manner, the information storage device can, for example, provide data to the controller for establishing the operating parameters of the pressure generating system, as well as accumulate compliance data regarding the use of the pressure support system.

In a further embodiment of the present invention, the slot and terminal are replaced with a transceiver operatively coupled to the controller, so that the information storage device communicates with the controller via the transceiver when the information storage device is proximate to the transceiver, thereby avoiding the need to physically place the information storage device in contact with the pressure support device. The controller reads information from the information storage device, writes information to the information storage device, or both via the transceiver.

In a still further embodiment of the present invention, an adapted that is configured to be disposed in the slot in the medical device is provided. The adapter, when provided in the slot in place of the information storage device, enables a variety of external devices, such as modem, a computer, or a communication device, to be operatively connected to the medical device, thereby enhancing the flexibility and ease of use of the pressure support system without adding dedicated communication links specific to each type of external device to be used.

It is yet another object of the present invention to provide an information storage device for use with a medical device, such as a pressure support system, to control its operation. In this embodiment of the present invention, the information storage device includes an identification storage area adapted to contain at least one of (a) information describing the information storage device itself, (b) information identifying a user to which the information storage device is assigned, and (c) information identifying a medical device assigned for use with the information storage device. The information storage device also includes an operating information storage area adapted to contain operating information for use in controlling the operation of the medical device.

It is yet another object of the present invention to provide an information storage device that receives and stores information from the medical device. In this embodiment of the present invention, the information storage device includes an identification storage area adapted to contain at least one of (a) information describing the information storage device itself, (b) information identifying a user to which the information storage device is assigned, and (c) information identifying a medical device assigned for use with the information storage device. The information storage device also includes a data storage area adapted to store data written thereon by the medical device. In this manner, compliance data regarding the use of the medical device, for example, can be stored on the information storage device. The information storage device is readily removeable from the medical device and can be provided to a monitoring center by simply mailing it to the monitoring center so that the compliance data can be downloaded, reviewed, analyzed and disseminated where appropriate.

It is yet another object of the present invention to provide a method of communicating with a medical device to establish the operating parameters of the medical device, accumulate compliance data regarding the use of the pressure support device, or both, and that does not suffer from the disadvantages associated with conventional techniques. This object is achieved by providing a method that includes (a) providing a medical device having a slot defined in an exterior surface, (b) providing an information storage device that can be disposed in the slot, (c) inserting the information storage device into the slot, and (d) communicating information from the information storage device to the medical device or vice versa when the information storage device is in the slot. In this manner, the information storage device provides data to the controller for establishing the operating parameters of the medical device as well as accumulate compliance data regarding the usage of the pressure support device.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 4 is a schematic diagram illustrating various embodiments for the prescription data block in the information storage device of FIG. 3;

DETAILED DESCRIPTION OF THE PRESENTLY PREFERRED EMBODIMENTS OF THE INVENTION

Figure 1:
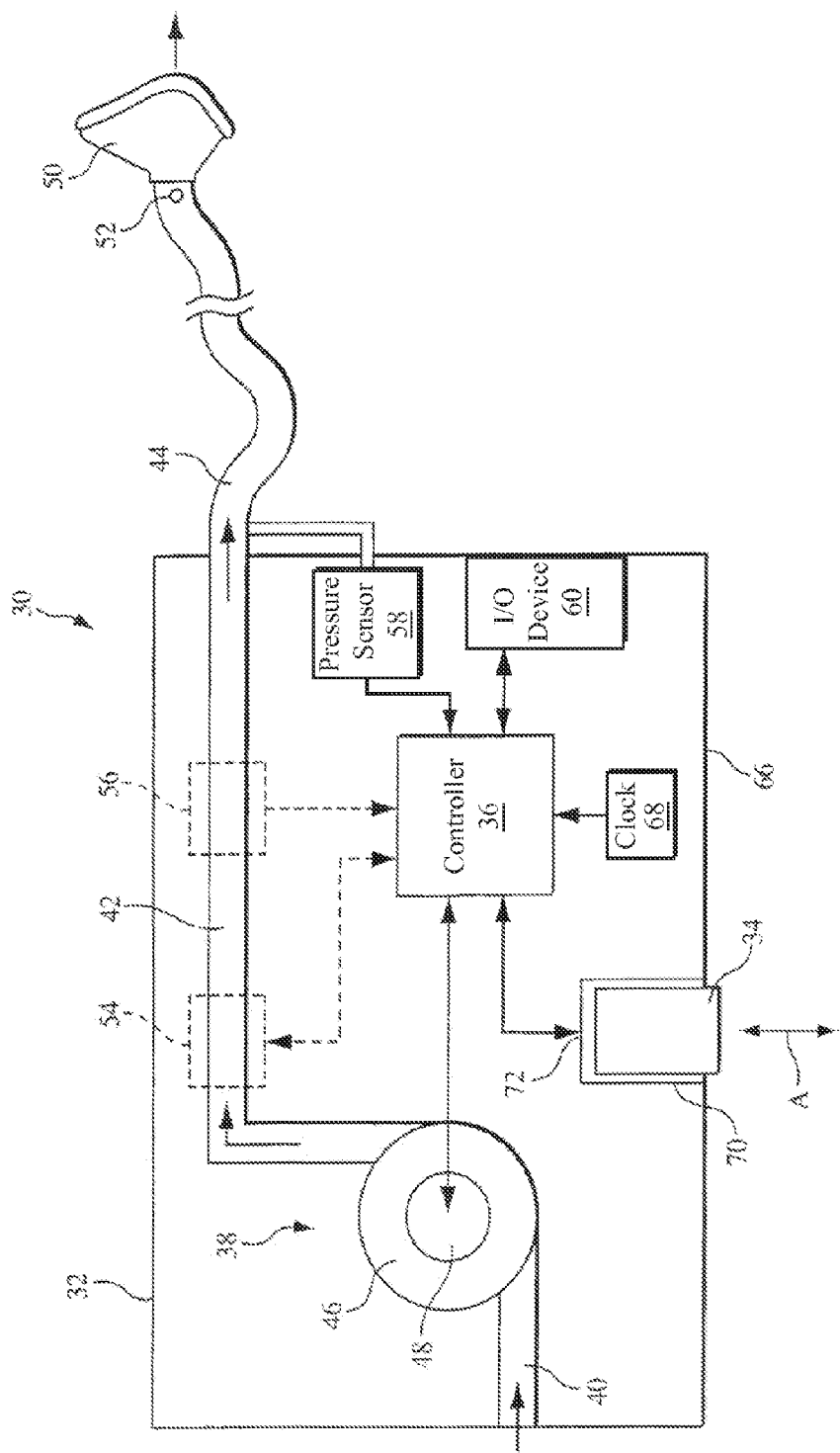
FIG. 1 is a schematic diagram of a pressure support system including an information storage device according to the principles of the present invention.
Figure 2:
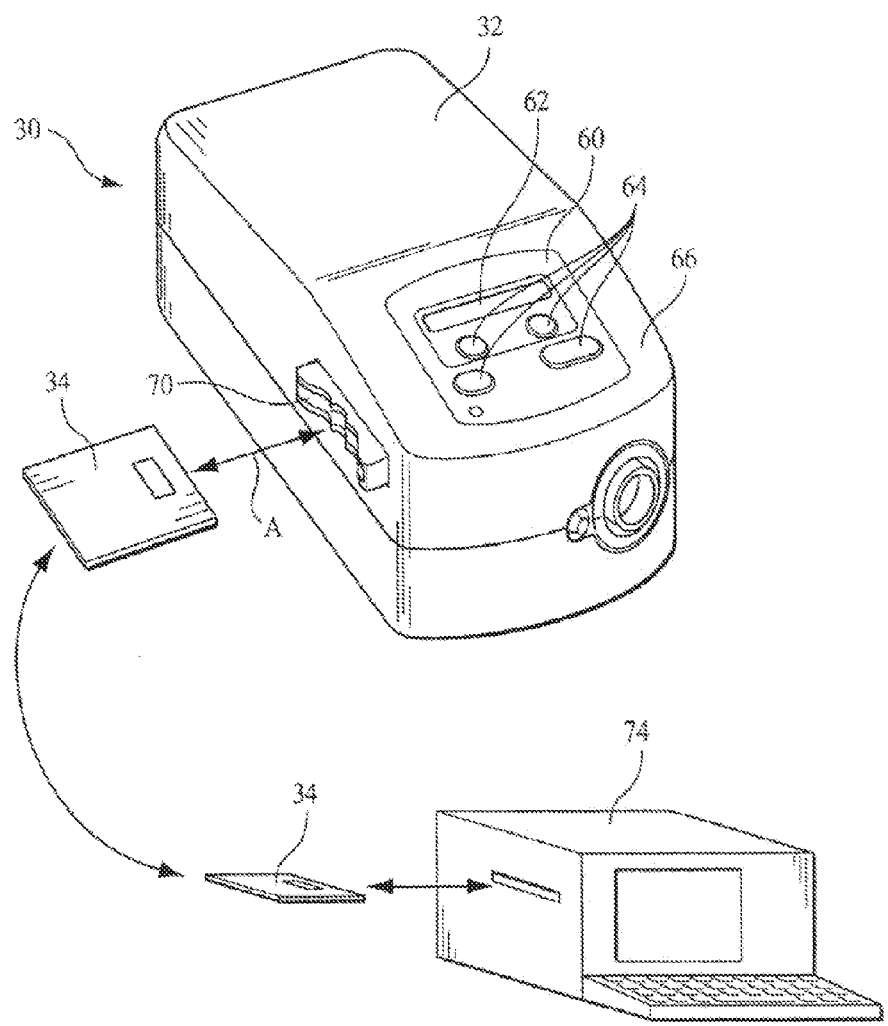
FIG. 2 is a front perspective view of a pressure support device, information storage device, and a remote monitoring/programming center according to the principles of the present invention.

FIG. 1 schematically illustrates an exemplary embodiment of a pressure support system 30 according to the principles of the present invention. Pressure support system 30 includes a pressure support device 32 that generates a flow of breathing gas at an elevated pressure and an information storage device 34 that communicates with a controller 36 in pressure support device 32. As discussed in greater detail below, data, instructions, information, or commands from information storage device 34, in one embodiment of the present invention, are used to control the operation of the pressure support device. In addition, data or information from the pressure support device can be stored in the information storage device. Furthermore, the present invention contemplates that both of these functions can be performed so that information storage device 34 acts as a convenient and simple means for transferring information and/or instructions to or from the pressure support system. The details of information storage device 34 and its interaction with the pressure support device to achieve these functions are discussed below.

Pressure support device 32 includes a pressure generator, generally indicated at 38, that receives a supply of breathing gas from a breathing gas source, such as ambient atmosphere in the illustrated embodiment, and creates a flow of breathing gas at a pressure greater than the ambient atmospheric pressure. An inlet conduit 40 communicates breathing gas from the gas source to the inlet of pressure generator 38. An exit conduit 42 communicates the flow of breathing gas from pressure generator 38 to a patient circuit 44, which delivers the elevated pressure breathing gas to the airway of a patient. In the illustrated embodiment, pressure generator 38 is a centrifugal blower in which a fan or impeller 46 is driven by a motor 48 operating under the control of controller 36. It is to be understood, that the present invention contemplates other techniques for generating a flow of breathing gas at an elevated pressure. For example, drag compressor, fan, piston, or bellows, can also be used as pressure generator 38 to create the flow of breathing gas at a pressure greater than the ambient atmospheric pressure.

In the illustrated embodiment, patient circuit 44 is a single-limb conduit having one end coupled to pressure support device 32 and a patient interface device 50 coupled to the other end. Patient interface 50 connects the conduit with the airway of the patient so that the elevated pressure gas flow is delivered to the patient's airway. Examples of patient interface devices include a nasal mask, nasal and oral mask, full face mask, nasal cannula, oral mouthpiece, tracheal tube, endotracheal tube, or hood. Because patient circuit 44 in the illustrated embodiment is a single-limb circuit, an exhalation port, 52 also referred to as an exhalation vent, exhaust port, or exhaust vent, is provided in the conduit to allow expired gas from the patient to exhaust to atmosphere. The present invention also contemplates that exhalation port 52 can be provided in the patient interface device in addition to or in the alternative to providing the port in the patient circuit.

The present invention further contemplates that the patient circuit is a conventional two-limb patient circuit. In which case, the exhalation port is eliminated. In a typical two-limb circuit, an exhaust conduit is coupled to the patient interface as the second limb, and an exhaust valve, which operated under the control of controller 36, is provided in the exhaust conduit to control the flow of exhaust gas from the patient circuit.

There are several techniques for controlling the pressure or flow of breathing gas to the patient provided by pressure support device 32. One such method involves providing a pressure controller 54 in exit conduit 42 to exhaust a portion of the breathing gas in the exit conduit to atmosphere or to the inlet of pressure generator 38, restrict the flow of breathing gas through the exit conduit, or a combination of these two functions. Controller 36 directs the operation of pressure controller 54 to regulate the pressure or flow of breathing gas provided to the patient. Examples of suitable pressure controllers are taught in U.S. Pat. No. 5,694,923 to Hete et al. and U.S. Pat. No. 5,598,838 to Servidio et al.

It is also known to control the speed of motor 48 so that pressure generator 38 outputs the breathing gas at the desired flow or pressure. This motor speed control technique can be used alone to control the flow or pressure of the breathing gas provided to the patient, or it can be used in combination with a pressure controller 54, such as those discussed above. For present purposes, the combination of a pressure generator 38 and any of the above described techniques for controlling the flow or pressure of breathing gas provided to the patient, e.g., motor speed control, a pressure controller, or both, are referred to as a "pressure generating system," with the ultimate goal of the pressure generating system being to provide breathing gas to the airway of the patient at the desired pressure or flow.

The present invention contemplates that pressure support system 30 can, if needed, include at least one sensor capable of measuring a characteristic associated with the flow of breathing gas, the pressure of the breathing gas, a condition of a patient using the pressure support system, a condition of the pressure support system, or any combination thereof. For example, FIG. 1 schematically illustrates a flow sensor 56 associated with exit conduit 42 and a pressure sensor 58 associated with patient circuit 44. The output from such sensors are provided to controller 36 and used to control the rate of flow and/or pressure of the breathing gas delivered to the patient. For example, in a bi-level pressure support system, the change between IPAP to EPAP and EPAP to IPAP is triggered based on the changes in the patient's breathing cycle, which is detected by such sensors. For an auto-titration pressure support system, the output of one or more such sensors is used to determine when to raise and lower the pressure provided to the patient, and can be used to determine the magnitude of the change in pressure. For example, U.S. Pat. No. 5,645,053 to Remmers et al., the content of which is again incorporated herein by reference, monitors patient flow to determine when and how to adjust the pressure applied to the patient.

It should be noted that the location and number of such sensors can be other than that shown in FIG. 1, so long as the function of providing feedback for the control of the pressure support system is achieved. In addition, it is also known to monitor the operation of the pressure generator to determine the condition of the patient, such as whether the patient in breathing on the system. In which case, the functions of the pressure and/or flow sensors are effectively incorporated into the pressure generator monitoring function.

Although sensors 56 and 58 are described above as being a flow and pressure sensor, respectively, it is to be understood that other types of sensors can be used in pressure support system 30. For example, a microphone can be provided to detect sounds produced by the patient, which can be used, for example, in an auto-titration pressure support system to control the pressure of the breathing gas delivered to the patient. See, e.g., U.S. Pat. Nos. 5,203,343 and 5,458,137 both to Axe et al., the contents of which are again incorporated herein by reference. Other sensors that can be used with the pressure support system include a temperature sensor that senses the temperature of gas anywhere in the breathing circuit, a current and/or voltage sensor for sensing the current/voltage of the signal provided to motor 48, and a tachometer that detects the rotational speed of motor 48. These sensors are used, for example, to sense the condition of the patient, the flow or pressure of gas provided to the patient, or the operation of the pressure support system. Still other external sensors can include EMG electrodes provided on the patient, a respiratory belt that measures movement of the chest and/or abdomen, and a motion sensor to detect patient movement, such a leg movement.

In the illustrated exemplary embodiment, pressure support system 30 includes an input/output device 60 for communicating information to the user and for communicating information or commands to controller 36. An example of input/output device 60 is an LCD or LED display 62 and manually actuated buttons 64 provided on a housing 66 of pressure support device 32. Of course, the present invention contemplates other types of input/output devices, such as a keypad, voice activated input device, audio outputs, lights, switches, and knobs for use in providing between the user and the pressure support device. In addition, a computer or printer terminal coupled to controller 36 can also constitute input/output device 60.

In an exemplary preferred embodiment of the present invention, pressure support system 30 also includes a clock 68 operatively coupled to the controller for use in keeping track of the use of the pressure support system. Clock 68 can be a conventional clock or any device that is capable of being used as a timing mechanism, preferably for keeping track of the amount of time the pressure support device is being used by the patient. If necessary, clock 68, controller 36, or both, can include a battery backup so that the operation of these devices or the information stored therein is not lost even if power to the pressure support device is interrupted.

As noted above, pressure support system 30 includes information storage device 34 that communicates with a controller 36. In an exemplary embodiment of the present invention, information storage device 34 is a so called "smart card" that contains a readable memory, a data storage area, or a combination of the two. Of course, information storage device 34 can also include an integrated circuit to provide the smart card with additional independent processing capabilities, such as performing diagnostic routines on the pressure support device, analyze the data provided to the information storage device, increasing the processing capability of controller 36, or any other function capable of being performed by a processor. In a preferred embodiment of the present invention, information storage device 34 is approximately the size, weight and shape of a conventional credit card so that it can be easily transported by a patient and sent to or from the patient via U.S. mail or other conventional postal-type carriers.

Information storage device 34 selectively inserts, as indicated by arrow A, into a slot 70 provided in housing 66 of pressure support device 32. A terminal 72 is provided within slot 70 so that the information storage device communicates with controller 36 when the information storage is properly disposed in the slot. As discussed below, controller 36 is capable of reading information from information storage device 34, writing information to the information storage device, or both. Terminal 72 is any conventional device capable of communicating with a smart card. As known to those skilled in the art, terminal 72 can include power couplings for providing power to the information storage device, where appropriate.

The present invention also contemplates that information storage device 34 is a conventional computer disc, such as a floppy disc, CDROM, or DVD storage device. In which case, terminal 72 includes the appropriate magnetic, electrical, or optical data accessing system for reading information from the disc, writing information to the storage device, or both.

One embodiment of the present invention contemplates that information storage device 34 provides the operating mode, operating parameters, or both for the pressure support system to controller 36. This embodiment enables the information storage device to be programmed at a remote location 74, such as at a pressure support monitoring/programming center, using an appropriate card programming device. For example, depending on the mode of pressure support that can be provided by the patient's pressure support device, the patient's prescription CPAP, IPAP, EPAP, or maximum/minimum pressure can be stored on the information storage device at the remote location and mailed to the patient. The patient merely inserts the information storage device into the slot in the pressure support system. Controller 36 reads the prescription pressure or pressures from the card and, thereafter, operates the pressure generating system to output a flow of breathing gas at the pressure level or within the pressure parameters specified on the information storage device. In a preferred embodiment of the present invention, the operating parameters read from the information storage device are stored in a memory (not shown) associated with controller 36 so that the information storage device can be removed and the pressure support device will continue to operate under the settings read from the information storage device, thereby eliminating the need for the information storage device once the pressure support device has been programmed.

Figure 3:
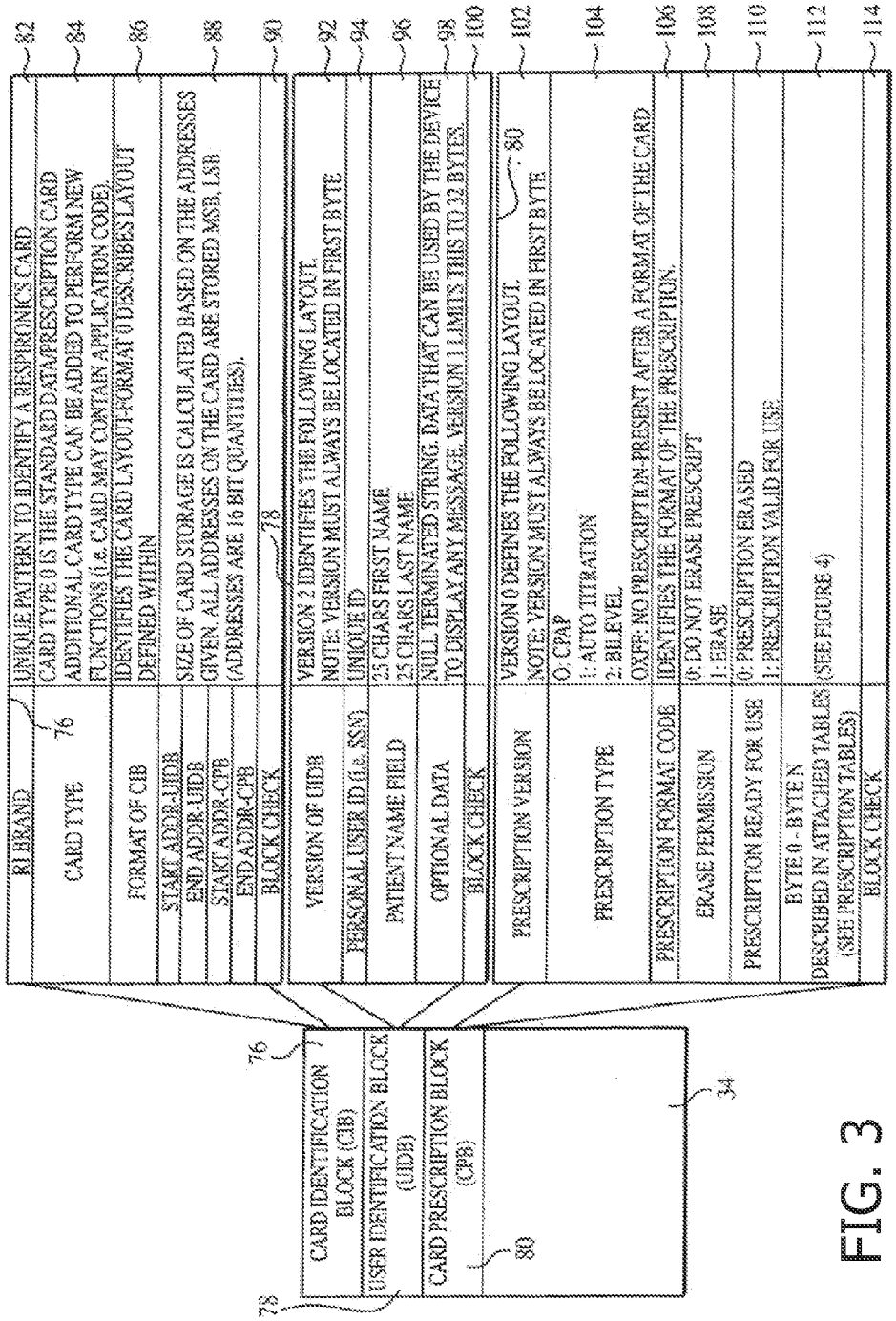
FIG. 3 is a schematic diagram illustrating one embodiment of the storage areas in the information storage device of FIGS. 1 and 2.

It can be appreciated that this embodiment of the present invention avoids the need for the pressure support device provider or other caregiver to travel to the patient's home to set up the operating parameters of the pressure support system or to change these parameters once the patient begins using the pressure support device. Nor does the patient have to return the entire device to the device provider for this purpose. Instead, the device provider or other caregiver merely sends the patient a new information storage device containing the new operating parameters. Alternatively, the patient can return the card to the device provider, who then reprograms the card at their operating center and returns it again to the patient. In either case, the burdens imposed on the patient and the device provider are greatly reduced as compared to the conventional method in which this is accomplished as discussed above. Furthermore, because only the device provider has the ability to change the operating parameters stored on the information storage device, the security for the settings, i.e., operating parameters, of the pressure support device is maximized, so that it is virtually impossible for the patient to intentionally or inadvertently alter the operating parameters of the pressure support device, especially their prescription pressure settings FIG. 3 is a detailed schematic diagram illustrating an exemplary embodiment of information storage device 34, and, in particular, the storage areas in the information storage device. Information storage device 34 in FIG. 3 is referred to as a "prescription card" because it contains information for setting the operating parameters of the pressure support device, and cannot receive data. In essence, it functions as a read-only memory card that sets the operating parameters of the pressure support device, which, in this embodiment, is the prescription pressure. It is to be understood that the present invention contemplates setting, modifying, activating, or deactivating or otherwise controlling any other operating parameter using information or commands stored on information storage device 34.

In an exemplary embodiment of the present invention, information storage device 34 includes the following three data storage areas: (1) a card identification block 76 that contains information describing the information storage device itself, (2) a user identification block 78 that contains information identifying a user to which information storage device 34 is assigned, and (3) a card prescription block 80 that contains contain prescription information for use in controlling the operation of such a pressure support system, such as the prescription pressure to be provided by the pressure support device. Of course, card prescription block 80 can contain information other than or in addition to prescription information for controlling other parameters or operations of the pressure support device.

In the illustrated embodiment, card identification block 76 includes a brand identification block 82 that contains information identifying the company associated with the card, such as the company that produced the card or that had the card produced on their behalf. A card type block 84 contains information identifying the type of information storage device. As noted above, information storage device 34 is a "prescription card" in that it only contains information for setting the operating parameters of the pressure support device. The present invention, however, contemplates the existence of other types of information storage devices, such as a "data/prescription card" shown in FIG. 5 and described in detail below, that can store data received from the pressure support system, as well as contain information for setting the operating parameters of the pressure support device. The type of card, e.g., "prescription card", "data/prescription card", or other type of card is identified in card type block 84.

Card identification block 76 also includes a card identification format block 86 that describes the format for the card identification block, i.e., how the data is arranged in the card identification block. It can be appreciated that the format for the information contained card identification block 76 need not be as shown in FIG. 3. In fact, there are numerous ways the information contained in card identification block 76 can be arranged. The purpose of card identification format block 86 is to identify the specific format for the card identification block being used in that information storage device. An address table block 88 in card identification block 76 defines the start and end addresses for user identification block 78 and card prescription block 80. In addition, card identification block 76 includes a check block 90 for error checking purposes.

It is to be understood that the information contained in card identification block 76 is not limited to that described above and shown in FIG. 3. On the contrary, other information, such as a unique card identification block that contains a card identification code unique to each information storage device, can be included in the card identification block. This card identification code may be helpful in identifying and tracking the information storage device. In addition, the present invention does not necessarily require that each block 82-90 described above be included in the card identification block, so long as the card identification block contains information describing the information storage device to which the information storage device is assigned.

In the illustrated exemplary embodiment, user identification block 78 includes a user identification format block 92 that describes the layout of the user identification block. As with the card identification block, it can be appreciated that the format for the information contained in user identification block 78 need not be as shown in FIG. 3. Therefore, the purpose of user identification format block 92 is to identify the specific format for the user identification block being used with that information storage device.

User identification block 78 also includes a user identification code block 94 and a user name block 96. User identification code block 94 contains at least one alphanumeric character that identifies a user to which the information storage device is assigned. For example, the user's social security number or a personal identification number (PIN) assigned by the card provider or the pressure support device provider may be stored in this block. User name block 96 contains information regarding a name of the user to which information storage device 34 is assigned. Preferably, the information contained in user identification code block 94, alone or in combination with the patient name information contained in user name block 96, uniquely identify a user to which information storage device 34 is assigned.

The information contained in user identification block 78 can be used for security purposes. For example, a pressure support device can be programmed to operate only if the proper user identification is provided in user identification code block 94, user name block 96, or both. This ensures that the patient is using only the pressure support device prescribed by the caregiver or prevents others from using that pressure support device.

In the illustrated embodiment, user identification block 78 includes a display data storage block 98 that contain information to be displayed on the pressure support system. For example, display data storage block 98 can contain a personalized greeting that is displayed on the input/output terminal of the pressure support device when the information storage device is inserted into the slot in the pressure support device. This serves, for example, to notify the user that the information storage device has been correctly inserted into the slot and that he or she is using the correct information storage device. The present invention also contemplates that other information, such as information on the patient's medical condition, treatments, as well as advertisements can be stored on the information storage device and displayed to the user via input/output device 60. User identification block 78 includes a check block 100 for error checking purposes.

It is to be understood that the information contained in user identification block 78 is not limited to that described above and shown in FIG. 3. On the contrary, other information, such as information identifying a pressure support device assigned to the patient, can be included in the card identification block. In addition, the present invention does not necessarily require that each block 92-100 described above be included in the user identification block, so long as the user identification block contains information identifying the user to which the information storage device is assigned.

Card prescription block 80 includes a card prescription format block 102 that describes the layout of the card prescription block. As with card identification block 76 and user identification block 78, it can be appreciated that the format for the information contained in card prescription block 80 need not be as shown in FIG. 3. The purpose of card prescription format block 92 is to identify the specific format for the card prescription block being used in that information storage device.

Card prescription block 80 further includes an operating mode identification block 104 that identifies the type of pressure support prescribed for the user. For example, operating mode identification block 104 may contain operating mode information identifying the mode of pressure support to be provided as being CPAP, bi-level, auto-titration, PAV or PPAP, or a combination thereof. It should be noted that this list of possible pressure support modes is not intended to be exhaustive and can include variations of these and other operating modes. This pressure support operating mode information is important because some pressure support devices may not be able to support certain modes of pressure support. For example, a relatively simple CPAP device is typically unable to provide bi-level, PPAP or PAV pressure support and cannot operate as an auto-titration pressure support system. If, for example, an information storage device in which operating mode identification block 104 specifies that the operating mode of pressure support is bi-level, is inserted into such a CPAP device, it may not be able to operate in this prescription mode. Therefore, an error message or other alarm should be provided to the user.

On the other hand, a pressure support device may be capable of operating in more than one mode of pressure support. In which case, the operating mode information contained in operating mode identification block 104 instructs the pressure support system how to operate. For example, it is not uncommon for an auto-titration pressure support device or a bi-level device to be able to function as a CPAP device. The information contained in prescription identification block 104 would determine whether such a pressure support system would operate as a CPAP device or as a bi-level or an auto-titration device.

The present invention also contemplates that a pressure support system can be produced that includes all of the necessary hardware for operating in a variety of pressure support modes. This enables a commonly designed, and preferably mass produced, pressure support system, each of which includes the same hardware, to be provided to a large number of patient regardless of the specific mode of pressure support each patient is to receive. The specific operating mode for each "generic" pressure support system can then be selected and altered, as needed, based on the operating mode information contained on the information storage device.

The present invention contemplates that when the information storage device is first produced, it is preferable that operating identification block 104 not specify any operating mode at all, so that the information storage device will only function as a prescription card after it has been appropriately programmed. For this reason, the present invention also contemplates that operating mode identification block 104 can contain information specifying that no operating mode is assigned.

Card prescription block 80 also includes a prescription format code block 106 that further identifies or describes the type of pressure support prescribed to the patient. For example, there are several techniques for performing the auto-titration mode of pressure support; one based on the sounds produced by the patient, and one based on the pressure and/or flow of gas in the patient circuit. Prescription format code block 106 is used, for example, to specify which of these variations for the auto-titration mode of pressure support is to be provided to the patient. It is to be understood, that prescription format code block 106 can be eliminated if prescription identification block 104 contains sufficient information to distinguish between these versions of the auto-titration mode of pressure support, for example.

Card prescription block 80 includes an erase permission block 108 and a ready for use block 110. Erase permission block 108 contains information for controlling whether the prescription information contained in the card prescription block can be erased. The information contained in erase permission block 108 effectively locks or unlocks the ability to alter the pressure support system operating parameters stored in information storage device 34.

Ready for use block 110 contains information for controlling whether the prescription information can be read from the information storage device. For example, if controller 36 in FIG. 1 sees a zero flag in this block, it will not read the prescription information contained in card prescription block 80. This feature of the present invention enables information storage device 34 to function as a one-time, read only prescription device, so that once the prescription information is read from the information storage device by the controller, this prescription information cannot be read again. This is accomplished by having the controller cause the data flag in ready for use block 110 to change to a zero after the prescription information is initially read from the information storage device by the pressure support device. One purpose of this feature of the present invention is to prevent unrestricted use of the information storage device.

Rather than have the controller not read the prescription information contained in card prescription block 80 if the information in ready for use block 110 indicates that the prescription information cannot be read, the present invention also contemplates allowing the controller to read the prescription information. However, if the information in ready for use block 110 indicates that the prescription information cannot be read, the controller is prevented from altering its operating parameters, which effectively accomplishes the same function as preventing the controller from reading the prescription information contained in card prescription block 80 in the first place.

The present invention also contemplates that information storage device 34 can be configured such that the information contained in ready for use block 110 always indicates that the prescription data can be read. In addition, the pressure support device can be prevented from causing ready for use block 110 to indicate that the prescription data cannot be read, e.g., preventing controller 36 from entering a zero flag in ready for use block 110. This enables a single information storage device to be used to set of the operating parameters of multiple pressure support devices. If, for example, the patient has a pressure support device at a primary residence and another pressure support device (or access to another pressure support device) at one or more secondary residences or temporary sleeping quarters, the patient need only carry the information storage device with them and use it to set up the same operating parameters on each device. With a conventional pressure support system, the patient would have to carry the pressure support device with them to be sure of having access to a suitably programmed pressure support system even when traveling far from home.

Card prescription block 80 includes a prescription information block 112 that contains the prescription information for establishing the operating parameters of the pressure support device. Details of prescription information blocks 112a, 112b and 112c suitable for use as prescription information block 112 are discussed below with reference to FIG. 4. Card prescription block 80 also includes a check block 114 for error checking purposes.

FIG. 4 illustrates various embodiments for the prescription information block 112 in the information storage device of FIG. 3. More specifically, prescription information block 112a illustrates the prescription information for a CPAP prescription, prescription information block 112b illustrates the prescription information for an auto-titration prescription, and prescription information block 112c illustrates the prescription information for a bi-level prescription. It should be understood that the prescription information for other modes of pressure support, such as PAV and PPAP, are omitted for the sake of brevity. In general, however, the prescription information block contains information for setting one of more of the operating parameters for the pressure support device.

Prescription information block 112a for a CPAP prescription includes a CPAP pressure block 116, which contains information defining the prescribed CPAP pressure. Prescription information block 112a for a CPAP prescription also includes a ramp shape block 118 and a ramp time block 120. Ramp shape block 118 contains information defining whether a ramp is provided and if so, the shape for the ramp. Ramp time block 120 contains information defining the duration of the pressure ramp.

As noted above, a pressure ramp is a feature in which a relatively low pressure is delivered to the patient at the outset of the pressure support therapy, and increases over the course of the therapy, typically over a period of 0-45 minutes, until the prescribed pressure level is reached. The pressure ramp features allows the patient to be presented with a relatively low pressure while falling asleep and presented with the prescription pressure once asleep. Data defining the duration or time period of the ramp is contained in ramp time block 120 and data defining the shape for the ramp is contained in ramp shape block 118. U.S. Pat. No. 5,682,878 to Ogden et al., the contents of which are incorporated herein by reference, describes the pressure ramp feature and multiple ramps shapes that can be provided to the patient.

Although ramp time block 118 sets a range of 0-45 minutes for the pressure ramp, it should be understood that other time ranges can be specified. In addition, although ramp shape block 120 provides only two choices for the ramp shape, i.e., no ramp or a linear ramp, it is to be understood that other information defining other ramp shapes, such as those taught in U.S. Pat. No. 5,682,878, can be provided in ramp shape block 120.

It is also known to provide multiple ramp cycles during the course of the pressure support therapy. See, for example, U.S. Reissue Pat. No. Re. 35,294, U.S. Pat. Nos. 5,492,113, and 5,551,418 all to Estes et al., the contents of each of which is incorporated herein by reference. In addition, it is known that the latter ramp cycle or cycles need not have the same duration and shape as the preceding ramp cycle. For this reason, the present invention contemplates providing additional ramp time and ramp shape blocks in prescription information block 112a or at other locations in information storage device 34 for specifying the duration and shape of ramps cycles initiated after the initial ramp cycle in the same pressure support therapy session.

In the illustrated embodiment, prescription information block 112a for a CPAP prescription includes an auto on data block 122 and an auto off data block 124. Auto on is a feature of a pressure support system in which the pressure support device does not begin administering the pressure support therapy until the patient begin breathing into the patient interface device. Auto off is a feature of a pressure support system in which the pressure support device automatically ceases administering the pressure support therapy when the patient stops breathing into the patient interface device for a predetermined period of time. Auto on and auto off can be used separately or together to control the operation of the pressure support system. U.S. Pat. No. 5,551,418 to Estes et al. describes the auto on and auto off features. The information contained in auto on data block 122 determines whether the auto on feature is enabled or disabled, and the information contained in auto off data block 125 determines whether the auto on feature is enabled or disabled.

Prescription information block 112b for an auto-titration prescription includes a maximum pressure block 126, which contains information defining the maximum pressure that can be output by the pressure support system during the pressure support therapy. Prescription information block 112b also includes a minimum pressure block 128, which contains information defining the minimum pressure that can be output by the pressure support system. Prescription information block 112b, like block 112a, also includes an auto on data block 122 and an auto off data block 124.

Prescription information block 112c for a bi-level prescription includes an IPAP pressure block 130 and an EPAP pressure block 132. IPAP pressure block 130 includes information defining the prescribed IPAP pressure, and EPAP pressure block 132 includes information defining the prescribed EPAP pressure. As with prescription information block 112a for a CPAP prescription, prescription information block 112c for a bi-level prescription includes ramp shape block 118' and ramp time block 120. Prescription information block 112b, like block 112a, also includes an auto on data block 122 and an auto off data block 124.

As discussed in U.S. Pat. No. 5,551,418, the IPAP, EPAP, or both can be controlled in a ramp fashion, just as with the CPAP. Ramp shape block 118' contains information defining the shape for the change in the IPAP, EPAP or both during the ramp cycle. For example, the linear ramp selection in ramp shape block 118' results in a linear increase in IPAP over the course of the ramp cycle with no change in the EPAP. The bi-level ramp selection results in a linear increase in both IPAP and EPAP during the ramp cycle. It can be appreciated that a great number of ramp shapes for IPAP and EPAP are possible, and information for selecting these ramp shapes can be provided in ramp shape block 118'. Of course, controller 36 must be programmed to control the pressure provided to the patient in the manner identified in ramp shape blocks 118 and 118'.

While the present invention contemplates controlling the operating parameters, such as the pressure support mode, prescription pressure, pressure ranges, ramp shape and duration, auto on and auto off, it is to be understood that other operating parameters can be modified, controlled or set using the information contained in the information storage device. For example, in a PAV or PPAP mode of pressure support, the degree or percentage of breathing assistance is set as an operating parameter for the pressure support device.

A further embodiment of the present invention contemplates enabling or disabling a timed backup breath feature based on the information, instructions or commands contained in the information storage device. When enabled, the timed back-up breath feature causes the pressure support device, operating in a bi-level mode of pressure support, to deliver an inspiratory flow of breathing gas to the patient automatically if the patient has not spontaneously initiated an inspiratory effort after a predetermined period of time. This is accomplished by providing a timer in the pressure support device. The breathing cycles of the patient are monitored in any conventional manner, and if the patient does not begin inspiring within a threshold time period, the pressure support device automatically delivers an inspiratory flow of breathing gas. This technique is used to treat, for example, central apneas. The level of the inspiratory pressure during the back up breath, the time limit before the back up breath is delivered, and the duration during which the inspiratory flow is delivered to the patient are examples of further operating parameters than can be input to the pressure support device via the information storage device.

A still further embodiment of the present invention contemplates storing advertisements, a survey or questionnaire, and/or other information that may be relevant to the patient or caregiver on the information storage device. The advertisements, a survey or questionnaire, and/or other information are read from the information storage device and displayed on input/output device 60. If a question or a survey is provided to the user, the answers to the survey and/or the scored results are stored on the information storage device for returning to the patient caregiver, either via the information storage device or via a communication link, such as the modem link discussed below. Presenting a questionnaire to a patient in conjunction with providing a medical treatment is taught, for example, in PCT Patent Application Publication No. WO 00/18347, the contents of which are incorporated herein by reference.

In addition, the present invention is not intended to require all of the above-described operating parameters to be set by the information storage device. For example, there may be a situation where auto on or auto off is not a feature available in a particular pressure support device. Therefore, the information storage devices designed for use with that type of pressure support device can omit the auto on and auto off data blocks. Also, one of more of the operating parameters of the pressure support device can be set manually, i.e., without using the information storage device, or pre-set in advance, with the remaining parameters or operating mode being set by the data or commands contained on the information storage device.

Figure 5A:
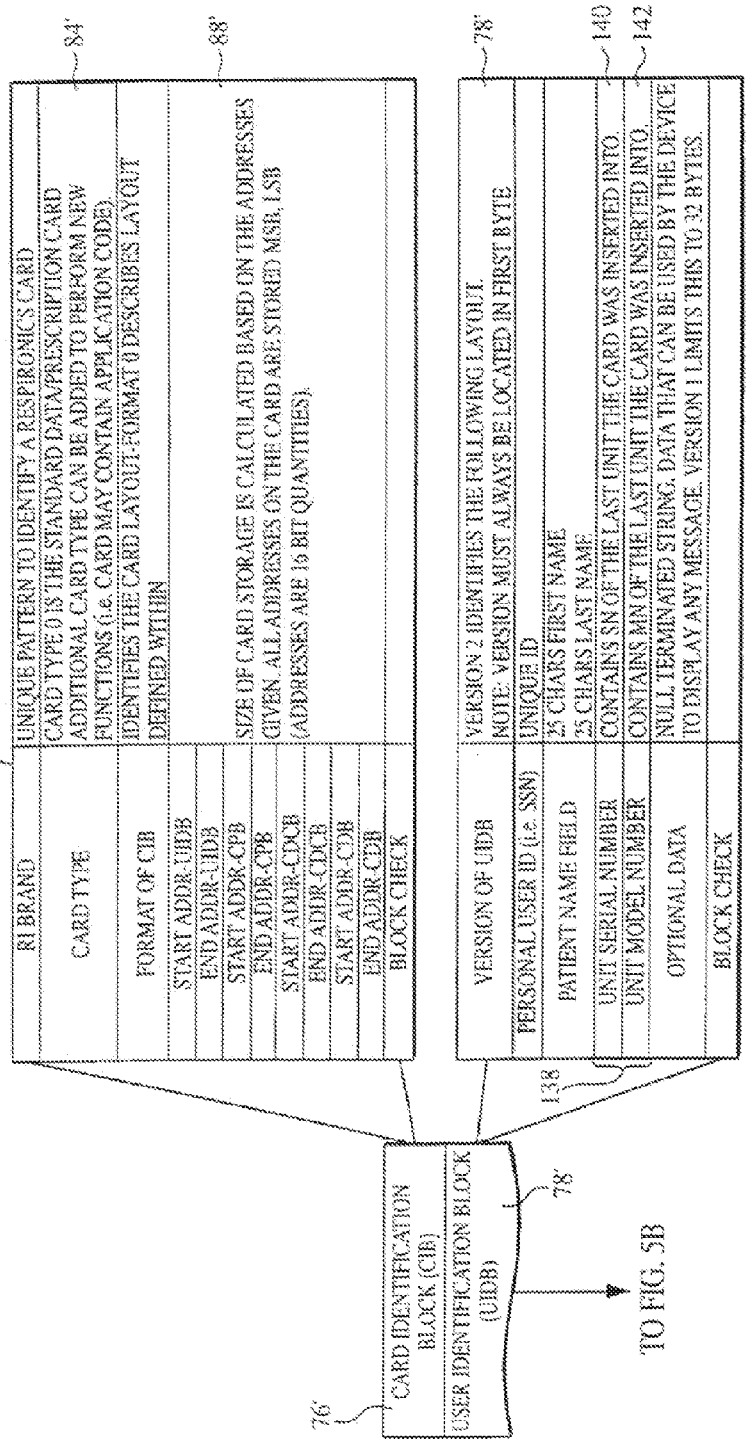
FIG. 5 is a schematic diagram illustrating an alternative embodiment for the storage areas in the information storage device of the present invention.
Figure 5B:
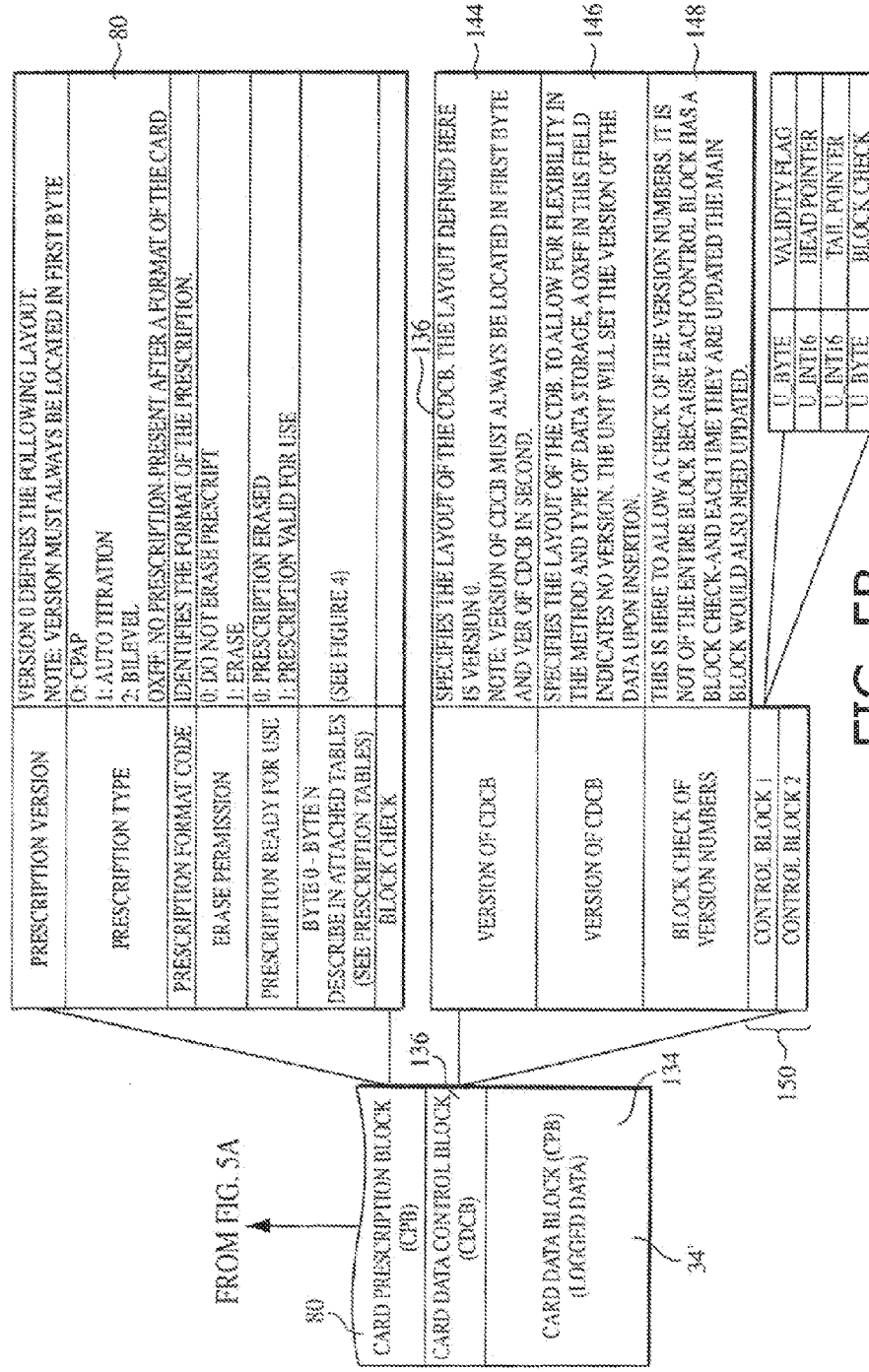

FIG. 5 is a detailed schematic diagram illustrating another exemplary embodiment of an information storage device 34' for use in the pressure support system of the present invention. Information storage device 34' is similar to information storage device 34 of FIG. 3, except that information storage device 34' includes a data storage area 134. Information storage device 34' in FIG. 5 is referred to as a "prescription/data card" because it contains information for setting the operating parameters of the pressure support device, and can also receive data, such as compliance data regarding the use of the pressure support device. Information storage device 34' includes the following data storage areas: (1) a card identification block 76' that contains information describing the information storage device itself, (2) a user identification block 78' that contains information identifying a user to which information storage device 34 is assigned, (3) a card prescription block 80 contains prescription information for use in controlling the operation of the pressure support system, such as the prescription pressure to be provided by the pressure support system, and (4) a card data control block 136.

In most respects, the features of information storage device 34' are identical to the those described above with respect to information storage device 34. For this reason, the common features of these two storage devices are not discussed below. However, the differences between these two types of information storage devices are highlighted below.

Card identification block 76' includes a card type block 84' that contains information identifying the type of information storage device. As noted above, the type of information storage device 34' is a "prescription/data card", because it contains information for setting the operating parameters of the pressure support system and can receive and store data provided by the pressure support device. Card identification block 76' also includes an address table block 88' that is similar to address table block 88 except that it includes information that defines the start and end addresses for card data control block 136.

User identification block 78', unlike user identification block 78, includes a pressure support device identification section 138 that contains information identifying a pressure support system assigned for use with the information storage device. More specifically, pressure support device identification section 138 in the illustrated embodiment includes a unit serial number block 140 and a unit model number block 142. Unit serial number block 140 and a unit model number block 142 contain serial number information and model number information, respectively, that together uniquely identifying a pressure support system assigned for use with the information storage device. This information can be used for security purposes to ensure that only the authorized prescription card is used with a particular pressure support device. This information can also be used for tracking purposes to identify the pressure support device to which the card is assigned or vice versa.

Data control block 136 includes a data control block format block 144 that contains information identifying the layout or format for data control block 136. A data format block 146 contains information identifying the layout or format for data storage area 134. A check block 148 is provided for error checking purposes. In addition, data control block 136 includes control blocks 150 containing information regarding the blocks of data stored in the data storage area.

Because information storage device 34' includes card prescription block 80, it can be used in the same manner as information storage device 34 to set the operating parameters of the pressure support system. However, the present invention contemplates omitting the card prescription block so that the information storage device cannot be used to set the operating parameters of the pressure support system, but can be used to store information provided by the pressure support device, such as compliance data, diagnostic data, or any other information gathered by the pressure support system, including information regarding the condition of the patient. In which case, the information storage device may be referred to as "data card", because its purpose is to store information provided to it from the medical device. An example of "other information" that can be compiled by the information storage device includes data regarding the number of apneas experienced by the user the pressure support device during a pressure support therapy. This information can be useful in monitoring the effectiveness of the patient's pressure support therapy.

Because of its small size and ease of use, information storage device 34' can be easily and inexpensively mailed to a monitoring center. The monitoring center can download, compile and analyze the data stored thereon for use in monitoring the compliance and/or effectiveness of the pressure support therapy, for example. Because the monitoring center controls the input of data from the information storage devices they receive, the data processing requirements for compiling this data is minimized. As noted above, this information may be of interest to the entity paying for the pressure support device to be sure that the patient is actually using the pressure support system. However, it may also be useful for the patient's caregiver to assess the patient's wellbeing.

Figure 6:
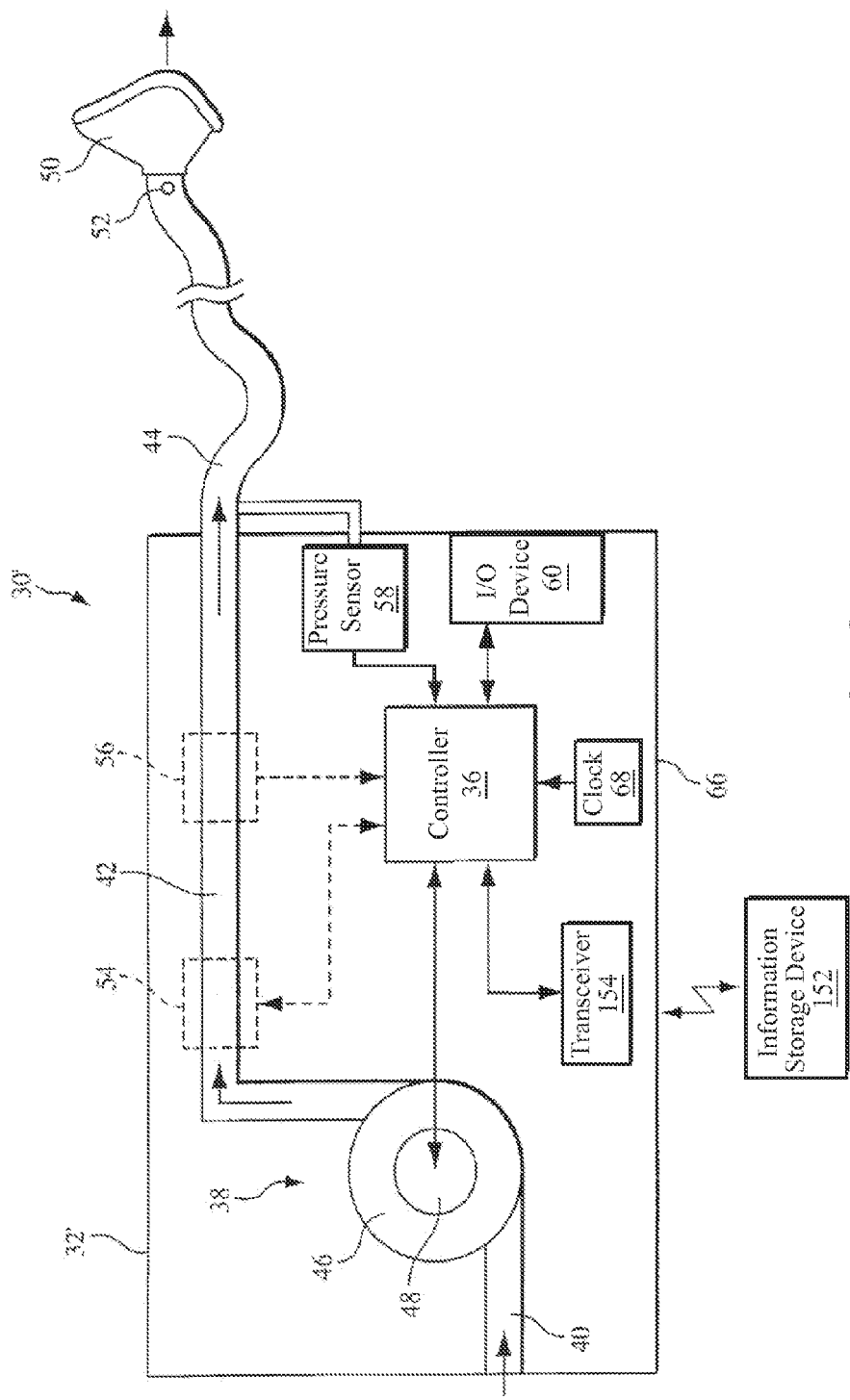
FIG. 6 is a schematic diagram of a further embodiment of a pressure support system according to the principles of the present invention.

In the embodiments described above, the information storage device is described as a smart card or other data storage medium that inserts into a slot provided in the exterior of the pressure support device. The present invention, however, contemplates other techniques for communicating between the pressure support device and the information storage device. For example, FIG. 6 illustrates a pressure support system 30' in which a so-called "contact-less" information storage device 152 communicates with pressure support device 32'. The pressure support system shown in FIG. 6 is identical to that shown in FIG. 1, except that instead of inserting the information storage device into a slot to communicate with controller 36, an antenna or other transceiver 154 is provided in place of the slot to communicate between controller 36 and information storage device 152 without the need for the information storage device to physically contact the pressure support device. This embodiment of the present invention enables controller 36 and the information storage device to communicate with one another merely by placing the information storage device in the vicinity of the pressure support system. The present invention contemplates that transceiver 154 can be any conventional device for transmitting data, information or commands to the information storage device, receiving data, information or commands, from the information storage device, or both. For example, transceiver 154 can be an RF, infrared, sonic, ultrasonic, or optical transmitter.

The present invention also contemplates that the transceiver can transmit energy to information storage device for powering any components of the information storage device that may require power. For example, it is known to use an electro-magnetic field to induce an electric current in a coil by inductive-coupling with the magnetic field. Of course, the present invention also contemplates providing a power source on the information storage device, such as a battery or solar cell, for powering the necessary components of the information storage device.

Figure 7:
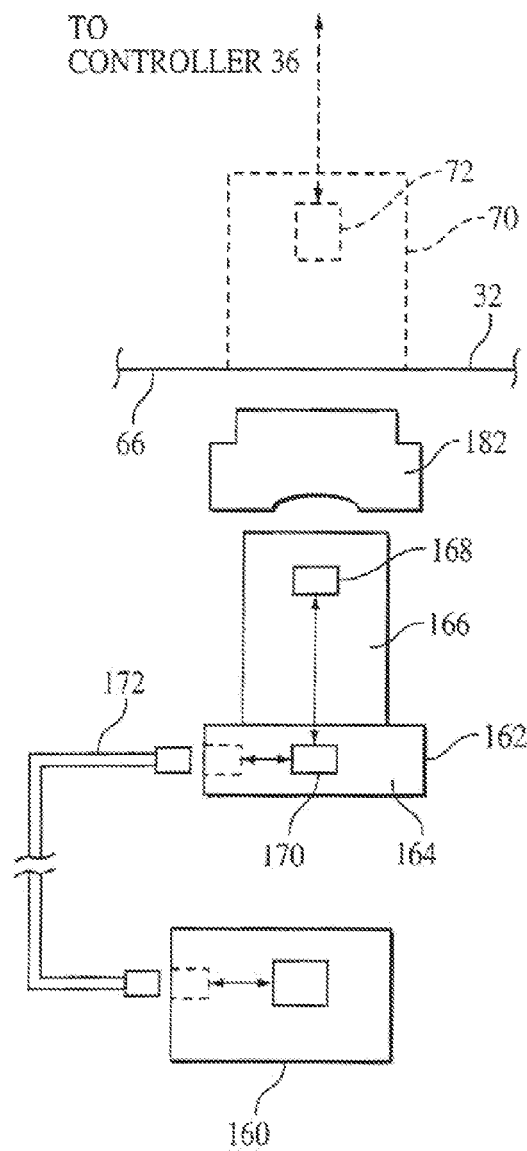
FIG. 7 is an exploded schematic diagram of a still further embodiment of a pressure support system according to the principles of the present invention.

As noted above, the present invention contemplates providing slot 70 in the body or housing 66 of pressure support device 32 to enable the controller or processor 36 and the smart card information storage device 34 to communicate with one another via a terminal 72. The present invention contemplates utilizing slot 70 and terminal 72 for other purposes in addition to providing a docking port for information storage device 34. In particular, the present invention contemplates using slot 72 to communicate between an external device 160 and the components of pressure support device, such as controller 36. See FIGS. 7-8.

To this end, the present invention contemplates providing an adapter 162 that is sized and configured to be disposed in slot 70. Adapter 162 includes an external interface portion 164 that remains outside slot 70 when the adapter is disposed in slot 70 and an internal interface portion 166 that inserts into slot 70. A terminal 168 is provided on internal interface portion that communicates with terminal 72 in slot 70. Depending on the function of adapter 162, an additional processing circuit 170 can be provided in adapter 162. A communication link 172 selectively connects adapter 162 member to external device 160.

Figure 8:
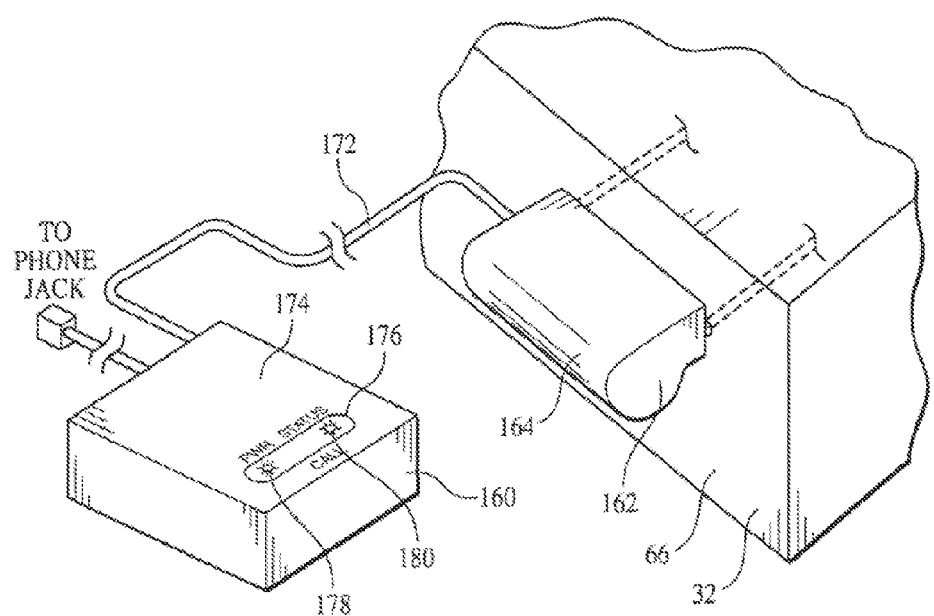
FIG. 8 is a perspective view of one possible implementation of the pressure support system shown in FIG. 7.

In the embodiment illustrated in FIG. 8, external device 160 is a modem 174 so that data, information, and/or instructions can be transmitted between a receiving station (not shown) and pressure support device 160. The data transmission link can be a dedicated telephone connection, internet, LAN, WAN, or any other data communication technique. This allows compliance information, for example, to be downloaded to a receiving station directly, and operating parameters, such as new prescription pressures, to be uploaded to the pressure support device, with a minimal amount of effort on the part of the patient or caregiver, while still providing the flexibility to use an information storage device to control the pressure support device and/or monitor its operation.

In a preferred embodiment of the present invention, modem 174 includes programming that enables the modem to automatically call a receiving station, for example, to routinely download information, such as patient compliance data, to the receiving station. The time of day to place the call and the frequency of the call, e.g., daily, every other day, weekly, etc., can be programmed into processing circuit 170 and/or into controller 36. In addition, modem 174 includes a manually actuated device 176, which, in the illustrated embodiment, is a button, for manually causing the modem to contact the receiving station.

The present invention further contemplates that modem 174 monitor certain exception criteria and call the receiving station based on an exception call parameter, e.g., immediately, with the next automatic call, first after hours opportunity, etc. Examples of exceptions that are monitored include:
  1) Pressure support device usage over a desired time period;
  2) Number of pressure support device on/off cycles over a desired time period;
  3) Number of pressure support device failures over a desired time period;
  4) Number of alarms, per type of alarm, over a desired time period;
  5) Number of device alerts, per type of alert, over a desired time period; and
  6) Survey or test scores presented to the patient on the pressure support device, as discussed above, falling outside a desired threshold.

The present invention contemplates that compliance data or other information can be stored in modem 174, for example on a dedicated EEPROM device, as done in information storage device 34. This allows for a seamless transition between using the smart card information storage device 34 and modem 174 with adapter 162, because the operating parameters of the modem can be initialized, loaded, and modified in the same manner done with the smart card information storage device.

In the embodiment shown in FIG. 8, modem 174 includes a first output device 178 in the form of a light provided on modem 174, to notify the user that power is being provided to the modem, which indicates that the modem has been properly installed. In addition, modem 174 preferably includes a status indication output device 180 that indicates when the modem is being used to communicate data between the medical device and the receiving station. It can be appreciated that output devices 178 and 180 are optional, their location can vary, and other visual or audio output devices can be provided on modem 174 to provide additional information to the user.

While a modem is contemplated as one external device that can be coupled to controller 36 in pressure support device 32 via slot 70, it can be appreciated that other external devices 160 can be coupled to controller 36 via slot 70. For example, a personal computer, palm or pocket computer or pocket organizer, printer, or any computer device can be coupled to the controller in pressure support device 32 by providing an appropriately configured adapter. In this configuration, adapter 162 effectively functions to convert the terminal 72 into an RS-232 terminal. This is especially helpful, for example, when conducting detailed or in depth monitoring of the patient via the pressure support device or when conducting diagnostic routines on the pressure support device. Perhaps more importantly, the need for a dedicated computer terminal, such as an RS-232 port is eliminated in favor of a multi-function port that can support both a smart card and an adapter.

A further embodiment of the present invention contemplates using adapter 162 to communicate the pressure support device with a wireless communication device, such as a satellite transceiver or a cellular telephone. This would allow the receiving station and pressure support device to remain in communication, for example, for uploading or downloading information and new operating parameters, even in situations where the pressure support device cannot be connected to a land-line system.

Figure 9:
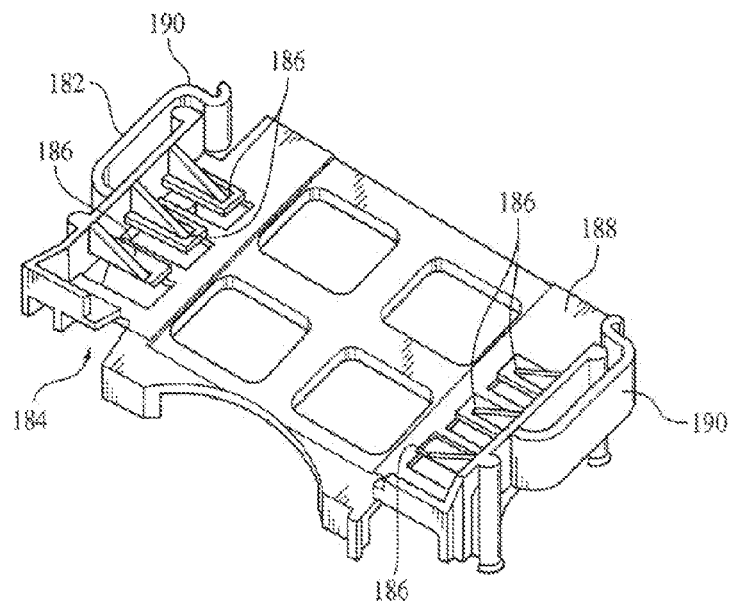
FIG. 9 is a perspective view of a retaining member adapted for use with the embodiment shown in FIGS. 7 and 8.

It can be appreciated that in the embodiment discussed above with respect to FIGS. 7-8, that a relatively large amount of hardware is physically located in or near slot 70 in pressure support device 32, which normally only holds the credit card sized information storage device. As a result, it is necessary to ensure that the hardware remains engaged within slot 70. To this end, the present invention contemplates providing a retaining member 182, shown in FIGS. 7 and 9, for maintaining a positive engagement between the information storage device and slot 70. In an exemplary embodiment of the present invention, retaining member 182 is permanently mounted within housing 66. It is to be understood, however, that retaining member 182 can be coupled to housing 66 in any manner, permanent or otherwise, so long as it increases the resistance to an item being pulled out of slot 70. Furthermore, the retaining member need not have the specific configuration shown in FIG. 9 so long as it accomplishes the function of providing a relative secure attachment between adapter 162 or any card-like insert and slot 70.

Retaining member 182 includes a slot, generally indicated 184, defined between first members 186 and second members 188 adapted to receive internal interface portion 166 of adapter 162 or information storage device 34. Flexible arms 190 are provided on opposing sides of slot 184. The end of each arm engages a notch (not shown) provided on each side of internal interface portion 166 or information storage device 34, thereby increasing the resistance to pull out of the internal interface portion 166 or information storage device 34 from slot 70.

In the embodiments discussed above, the information storage device is described for use in conjunction with a pressure support system. It is to be understood, however, that the present invention further contemplates using the information storage device as a means to communicate with and/or control the operation of other medical devices. For example, information storage device can be provided in a glucose monitor so that each time the patient checks his or her blood sugar level, the results are stored on the information storage device, which can then be sent to the caregiver for review or analysis. Other medical devices in which the above-described information storage device technique for communication can be used include: light therapy devices, magnetic therapy devices, pulse oximeters, blood gas analyzers, spirometers, oxygen concentrator, any monitor, such as an infant monitor. It is to be understood that this list is not intended to be exclusive or exhaustive.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A pressure support therapy system comprising:
    (a) a data transmission assembly located at a first location, comprising:
        (1) a data transmission housing,
        (2) a first electrical contact disposed at a first location on a first member of the data transmission assembly, and
        (3) a modem disposed in the data transmission housing, the modem being operatively coupled to the first electrical contact and adapted to communicate with a second location remote from the first location;
    (b) an information storage device, comprising:
        (1) an information storage housing,
        (2) a second electrical contact disposed at a first location on the information storage housing, and
        (3) a first storage element disposed on information storage housing operatively coupled to the second electrical contact; and
    (c) a pressure support system located at the first location, comprising:
        (1) a pressure support housing, wherein the data transmission housing is separate from and external to the pressure support housing,
        (2) a pressure generating system disposed within the pressure support housing for generating a flow of breathing gas,
        (3) a controller disposed within the pressure support housing and in communication with the pressure generating system, wherein the controller controls the operation of the pressure generating system such that a pressure of the flow of breathing gas remains substantially constant during at least a portion an inspiratory phase of a patient's respiratory cycle and corresponds to a pressure sufficient to treat obstructive sleep apnea,
        (4) a receiving port defined in an exterior surface of the pressure support housing, wherein the receiving port is sized and configured for selectively and individually receiving at least a portion of the first member of the data transmission assembly including the first electrical contact while the modem is operatively coupled to the first electrical contact and at least a portion of the information storage housing including the second electrical contact, and
        (5) a third electrical contact disposed in the receiving port, wherein the first electrical contact operatively couples to the third electrical contact responsive to the at least a portion of the first member of the data transmission assembly being disposed in the receiving port and wherein the second electrical contact operatively couples to the third electrical contact responsive to the at least a portion of the information storage housing being disposed in the receiving port.

2. The pressure support therapy system of claim 1, wherein the modem is a hardwired modem or a wireless modem.

3. The pressure support therapy system of claim 1, wherein data transmission assembly further comprises a second storage element disposed in the data transmission housing.

4. The pressure support therapy system of claim 1, wherein the pressure support system further comprises a second storage element disposed in the pressure support housing, and wherein the modem queries the second storage element responsive to the at least a portion of the first member of the data transmission assembly being disposed in the receiving port.

5. The pressure support therapy system of claim 1, further comprising at least one sensor adapted to measure a characteristic associated with one of: (1) a rate of the flow of breathing gas, (2) a pressure of the flow of breathing gas, and (3) a condition of a patient using the pressure support system, wherein an output of the sensor is provided to the controller.

6. The pressure support system of claim 1, wherein the pressure generating system includes:
    a pressure generator; and
    a pressure controller associated with pressure generator and operatively coupled to the controller for controlling 1) a pressure or 2) a rate of the flow of breathing gas delivered to the patient by the pressure generating system.

7. The pressure support system of claim 1, further comprising an input/output device operatively coupled to the controller.

8. The pressure support system of claim 1, further comprising a timing system operatively coupled to the controller for monitoring usage of the pressure support system.

9. The pressure support system of claim 1, wherein the first storage element on information storage device includes operating parameter information for the pressure support system, and wherein the operating parameter information is based on a patient circuit, patient interface device, or both to be operatively coupled to the pressure support system.

10. A pressure support system comprising:
    (a) a pressure support device comprising:
        (1) a housing,
        (2) a pressure generating system disposed within the housing for generating a flow of breathing gas,
        (3) a controller disposed within the housing in communication with the pressure generating system that controls the operation of the pressure generating system,
        (4) a receiving port defined in an exterior surface of the housing, and
        (5) an electrical contact dispose in the receiving port;
    (b) an information storage device adapted to be selectively disposed in the receiving port, the information storage device comprising:
        (1) an identification storage area adapted to contain information identifying at least one of (a) information describing the information storage device itself, and (b) information identifying a user to which the information storage device is assigned, and
        (2) at least one of (a) a first information storage area adapted to contain information for use in controlling an operation of the pressure support device, and (b) a data storage area adapted to store data written thereon by the pressure support device, and
    (c) an adapter adapted to be selectively disposed in the receiving port, wherein the adapter provides communication access between the controller and an electronic device external to the pressure support device responsive to the adapter being inserted into the receiving port, wherein the controller communicates with the information storage device via the electrical contact responsive to the information storage device being disposed in the receiving port, and wherein the controller is adapted to at least one of (a) read information from the information storage device and (b) write information to the information storage device via the electrical contact.

11. The pressure support system of claim 10, wherein the pressure support device further comprises a timing system operatively coupled to the controller for monitoring usage of the pressure support device.

12. The pressure support system of claim 10, wherein the first information storage area includes a first area containing operating mode information designating an operating mode of the pressure support device and operating parameter information designating an operating parameter of the pressure support device.

13. The pressure support system of claim 10, wherein the first information includes operating parameter information for the pressure support system, and wherein the operating parameter information is associated with a patient circuit, a patient interface device, or both a patient circuit and a patient interface device adapted to be coupled to the pressure support system.

* * * * *